(12) United States Patent
Campbell et al.

(10) Patent No.: US 10,309,930 B2
(45) Date of Patent: Jun. 4, 2019

(54) DYNAMIC ORTHOGONAL ANALYSIS METHOD

(71) Applicant: DH Technologies Development Pte. Ltd., Singapore (SG)

(72) Inventors: John Lawrence Campbell, Milton (CA); Eva Duchoslav, Toronto (CA); Yves Le Blanc, Newmarket (CA); David M. Cox, Toronto (CA)

(73) Assignee: DH Technologies Development Pte. Ltd., Singapore (SG)

( * ) Notice: Subject to any disclaimer, the term of this patent is extended or adjusted under 35 U.S.C. 154(b) by 171 days.

(21) Appl. No.: 15/516,387

(22) PCT Filed: Sep. 21, 2015

(86) PCT No.: PCT/IB2015/057260
§ 371 (c)(1),
(2) Date: Apr. 1, 2017

(87) PCT Pub. No.: WO2016/055886
PCT Pub. Date: Apr. 14, 2016

(65) Prior Publication Data
US 2017/0248548 A1 Aug. 31, 2017

Related U.S. Application Data

(60) Provisional application No. 62/061,490, filed on Oct. 8, 2014.

(51) Int. Cl.
*H01J 49/26* (2006.01)
*G01N 27/62* (2006.01)
*H01J 49/00* (2006.01)

(52) U.S. Cl.
CPC .......... *G01N 27/624* (2013.01); *H01J 49/004* (2013.01); *H01J 49/0031* (2013.01); *H01J 49/0036* (2013.01); *H01J 49/0045* (2013.01)

(58) Field of Classification Search
CPC ................ G01N 27/624; H01J 49/0031; H01J 49/0036; H01J 49/004; H01J 49/0045
(Continued)

(56) References Cited

U.S. PATENT DOCUMENTS

2003/0213900 A1 11/2003 Hoyes
2005/0253061 A1* 11/2005 Cameron ............. G01N 27/624
250/287
(Continued)

OTHER PUBLICATIONS

International Search Report and Written Opinion for PCT/IB2015/057260, dated Feb. 19, 2016.
(Continued)

*Primary Examiner* — Nicole M Ippolito
(74) *Attorney, Agent, or Firm* — John R. Kasha; Kelly L. Kasha; Kasha Law LLC (57) ABSTRACT

Systems and methods are provided for providing a DMS precursor ion survey scan. An ion source configured to receive a sample is instructed to ionize the sample using a processor. A DMS device configured to receive ions from the ion source is instructed to separate precursor ions received from the ion source and transmit precursor ions using two or more CoVs using the processor. A mass analyzer configured to receive transmitted precursor ions from the DMS device is instructed to measure the m/z intensities of the transmitted precursor ions across an m/z range at each CoV of the two or more CoVs using the processor. The measured m/z intensities of the transmitted precursor ions received from the mass analyzer are stored as a function of m/z value and CoV using the processor. This produces a stored two-dimensional mapping of m/z intensities of the precursor ions of the sample.

15 Claims, 7 Drawing Sheets

(58) Field of Classification Search
USPC .................................................. 250/281, 282
See application file for complete search history.

(56) References Cited

U.S. PATENT DOCUMENTS

| | | | |
|---|---|---|---|
| 2006/0060768 A1* | 3/2006 | Kaufman | H01J 49/42 250/281 |
| 2006/0289745 A1* | 12/2006 | Miller | G01N 27/624 250/294 |
| 2009/0261247 A1* | 10/2009 | Cooks | H01J 49/422 250/292 |
| 2012/0132795 A1 | 5/2012 | Duong et al. | |
| 2014/0291505 A1 | 10/2014 | Auger et al. | |

OTHER PUBLICATIONS

Tannu et al., "Two-Dimensional Fluorescence Difference Gel Electrophoresis for Comparative Proteomics Profiling." Journal of Nature Protocols, vol. 1, pp. 1732-1742, Nov. 16, 2006.

* cited by examiner

DYNAMIC ORTHOGONAL ANALYSIS METHOD

CROSS REFERENCE TO RELATED APPLICATION

This application claims the benefit of U.S. Provisional Patent Application Ser. No. 62/061,490, filed Oct. 8, 2014, the content of which is incorporated by reference herein in its entirety.

INTRODUCTION

Various embodiments relate generally to mass spectrometry, and more particularly to systems and methods for using orthogonal information from a differential mobility spectrometry (DMS) precursor ion survey scan in a tandem mass spectrometry workflow in order to make the workflow more efficient, more productive, and more amenable to limited sample volumes.

Tandem mass spectrometry, or mass spectrometry/mass spectrometry (MS/MS) is a well-known technique for analyzing compounds. Originally a tandem mass spectrometer was thought of as two mass spectrometers arranged in tandem. However, modern tandem mass spectrometers are much more complex instruments and may have many different configurations. Generally, however, tandem mass spectrometry, involves ionization of one or more compounds, selection of one or more precursor ions of the one or more compounds, fragmentation of the one or more precursor ions into product ions, and mass analysis of the product ions.

A large number of different types of experimental methods or workflows can be performed using a tandem mass spectrometer. Two broad categories of these workflows are information dependent acquisition (IDA) and data independent acquisition (DIA).

In an IDA workflow, the actions of the tandem mass spectrometer are varied from scan to scan based on data acquired in a previous scan. Data is analyzed as it is being acquired, and, based on this data, precursor ion masses are selected for fragmentation. In IDA, a user can set the criteria that activate the experiment and the method parameters that are used. Another name for IDA is data dependent acquisition.

In IDA, there are many different ways data can be acquired and analyzed in order to select the precursor ion masses for fragmentation. One way this data is acquired and analyzed is using a full scan ion survey scan. A precursor ion mass spectrum is obtained from a full scan ion survey scan. The most intense precursor ion peaks from the full scan ion mass spectrum are then selected for fragmentation, for example.

Qualitative mass spectrometry experiments are most commonly performed using an IDA workflow, where a survey scan is collected, and precursors are selected for MS/MS analysis based on a set of user defined criteria. This is widely applied for LC-MS/MS analyses in qualitative screening, semi-quantitative profiling, and compound identification experiments.

However, in proteomics, and many other sample types, the complexity and dynamic range of compounds is very large. This poses challenges for traditional IDA workflows, requiring very high speed MS/MS acquisition to deeply interrogate the sample in order to both identify and quantify a broad range of analytes. As a result, DIA workflows have been used to increase the reproducibility and comprehensiveness of data collection.

In a traditional DIA workflow, the actions of the tandem mass spectrometer are not varied from scan to scan based on data acquired in a previous scan. Instead a precursor ion mass range is selected. All precursor ions in that mass range are then fragmented, and all of the product ions of all of the precursor ions are mass analyzed. This precursor ion mass range can be very narrow, where the likelihood of multiple precursors within the window is small. Or, this window can be large, and the likelihood of multiple precursors within this window is high.

Other names for DIA can include, but are not limited to, MS/MS of all or a non-specific fragmentation method. SWATH™ acquisition is also a type of DIA workflow. In Swath acquisition, a precursor ion mass isolation window is stepped across a mass range. All the precursor ions in the mass isolation window are fragmented, and all of the product ions of all of the precursor ions in the mass isolation window are mass analyzed.

DIA workflows, however, are not without limitations. For example, the non-specific nature of these workflows means that product ion data is collected for every nominal mass-to-charge ratio (m/z) value in an arbitrary range of values. As a result, for samples with relatively few precursor ion spread across the mass range, a DIA workflow can be highly inefficient. For infusion-based experiments, for example, this inefficiency can prevent the use of a DIA workflow if the sample volume is limited.

SUMMARY

A system is disclosed for providing a differential mobility spectrometry (DMS) precursor ion survey scan. The system includes an ion source, a differential mobility spectrometry (DMS) device, a mass analyzer, and a processor in communication with the ion source and the DMS device, and the mass analyzer.

The ion source is configured to receive a sample and ionize the sample. The DMS device is configured to receive ions from the ion source and to transmit separated precursor ions based on a compensation voltage (CoV). The mass analyzer is configured to receive transmitted precursor ions from the DMS device and measure the mass-to-charge ratio (m/z) intensities of the transmitted precursor ions.

The processor instructs the ion source to ionize the sample and instructs the DMS device to separate precursor ions received from the ion source and transmit precursor ions using two or more CoVs. The processor further instructs the mass analyzer to measure the m/z intensities of the transmitted precursor ions across an m/z range at each CoV of the two or more CoVs and stores the measured m/z intensities of the transmitted precursor ions received from the mass analyzer as a function of m/z value and CoV, producing a two-dimensional mapping of m/z intensities of the transmitted precursor ions of the sample.

A method is disclosed for providing a DMS precursor ion survey scan. An ion source configured to receive a sample is instructed to ionize the sample using a processor. A DMS device configured to receive ions from the ion source is instructed to separate precursor ions received from the ion source and transmit precursor ions using two or more CoVs using the processor. A mass analyzer configured to receive transmitted precursor ions from the DMS device is instructed to measure the m/z intensities of the transmitted precursor ions across an m/z range at each CoV of the two or more CoVs using the processor. The measured m/z intensities of the transmitted precursor ions received from the mass analyzer are stored as a function of m/z value and CoV, producing a two-dimensional mapping of m/z intensities of the precursor ions of the sample using the processor.

A computer program product is disclosed that includes a non-transitory and tangible computer-readable storage medium whose contents include a program with instructions being executed on a processor so as to perform a method for providing a DMS precursor ion survey scan. The method includes providing a system, wherein the system comprises one or more distinct software modules, and wherein the distinct software modules comprise a control module.

The control module instructs an ion source configured to receive a sample to ionize the sample. The control module instructs a DMS device configured to receive ions from the ion source to separate precursor ions received from the ion source and transmit precursor ions using two or more compensation voltages (CoVs). The control module instructs a mass analyzer configured to receive transmitted precursor ions from the DMS device to measure the m/z intensities of the transmitted precursor ions across an m/z range at each CoV of the two or more CoVs. The control module stores the measured m/z intensities of the transmitted precursor ions received from the mass analyzer as a function of m/z value and CoV, producing a two-dimensional mapping of m/z intensities of the precursor ions of the sample.

These and other features of the applicant's teachings are set forth herein.

BRIEF DESCRIPTION OF THE DRAWINGS

The skilled artisan will understand that the drawings, described below, are for illustration purposes only. The drawings are not intended to limit the scope of the present teachings in any way.

Before one or more embodiments of the present teachings are described in detail, one skilled in the art will appreciate that the present teachings are not limited in their application to the details of construction, the arrangements of components, and the arrangement of steps set forth in the following detailed description or illustrated in the drawings. Also, it is to be understood that the phraseology and terminology used herein is for the purpose of description and should not be regarded as limiting.

DESCRIPTION OF VARIOUS EMBODIMENTS

Computer-Implemented System

Figure 1:
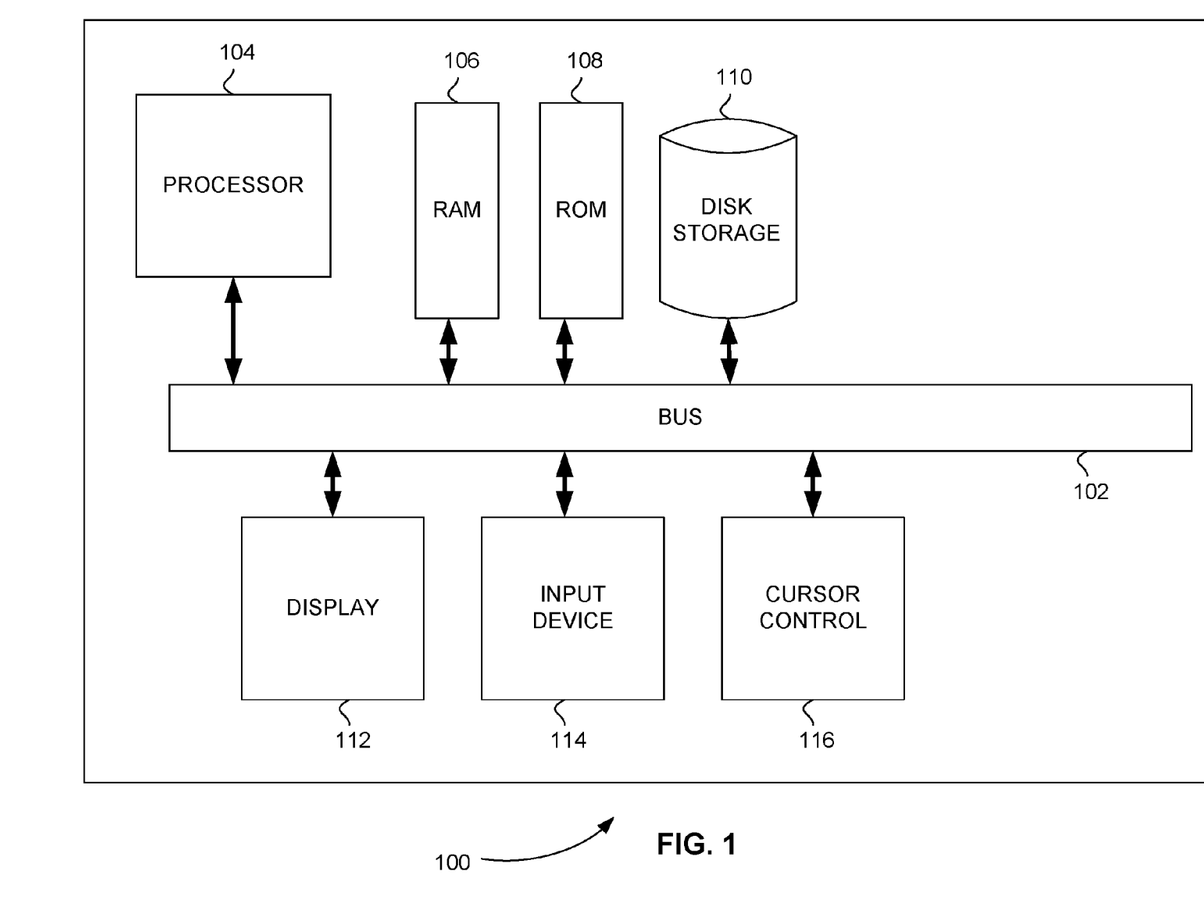
FIG. 1 is a block diagram that illustrates a computer system, upon which embodiments of the present teachings may be implemented.

FIG. 1 is a block diagram that illustrates a computer system 100, upon which embodiments of the present teachings may be implemented. Computer system 100 includes a bus 102 or other communication mechanism for communicating information, and a processor 104 coupled with bus 102 for processing information. Computer system 100 also includes a memory 106, which can be a random access memory (RAM) or other dynamic storage device, coupled to bus 102 for storing instructions to be executed by processor 104. Memory 106 also may be used for storing temporary variables or other intermediate information during execution of instructions to be executed by processor 104. Computer system 100 further includes a read only memory (ROM) 108 or other static storage device coupled to bus 102 for storing static information and instructions for processor 104. A storage device 110, such as a magnetic disk or optical disk, is provided and coupled to bus 102 for storing information and instructions.

Computer system 100 may be coupled via bus 102 to a display 112, such as a cathode ray tube (CRT) or liquid crystal display (LCD), for displaying information to a computer user. An input device 114, including alphanumeric and other keys, is coupled to bus 102 for communicating information and command selections to processor 104. Another type of user input device is cursor control 116, such as a mouse, a trackball or cursor direction keys for communicating direction information and command selections to processor 104 and for controlling cursor movement on display 112. This input device typically has two degrees of freedom in two axes, a first axis (i.e., x) and a second axis (i.e., y), that allows the device to specify positions in a plane.

A computer system 100 can perform the present teachings. Consistent with certain implementations of the present teachings, results are provided by computer system 100 in response to processor 104 executing one or more sequences of one or more instructions contained in memory 106. Such instructions may be read into memory 106 from another computer-readable medium, such as storage device 110. Execution of the sequences of instructions contained in memory 106 causes processor 104 to perform the process described herein. Alternatively hard-wired circuitry may be used in place of or in combination with software instructions to implement the present teachings. Thus implementations of the present teachings are not limited to any specific combination of hardware circuitry and software.

In various embodiments, computer system 100 can be connected to one or more other computer systems, like computer system 100, across a network to form a networked system. The network can include a private network or a public network such as the Internet. In the networked system, one or more computer systems can store and serve the data to other computer systems. The one or more computer systems that store and serve the data can be referred to as servers or the cloud, in a cloud computing scenario. The one or more computer systems can include one or more web servers, for example. The other computer systems that send and receive data to and from the servers or the cloud can be referred to as client or cloud devices, for example.

The term "computer-readable medium" as used herein refers to any media that participates in providing instructions to processor 104 for execution. Such a medium may take many forms, including but not limited to, non-volatile media, volatile media, and transmission media. Non-volatile media includes, for example, optical or magnetic disks, such as storage device 110. Volatile media includes dynamic memory, such as memory 106. Transmission media includes coaxial cables, copper wire, and fiber optics, including the wires that comprise bus 102.

Common forms of computer-readable media or computer program products include, for example, a floppy disk, a flexible disk, hard disk, magnetic tape, or any other magnetic medium, a CD-ROM, digital video disc (DVD), a Blu-ray Disc, any other optical medium, a thumb drive, a memory card, a RAM, PROM, and EPROM, a FLASH-EPROM, any other memory chip or cartridge, or any other tangible medium from which a computer can read.

Various forms of computer readable media may be involved in carrying one or more sequences of one or more instructions to processor 104 for execution. For example, the instructions may initially be carried on the magnetic disk of a remote computer. The remote computer can load the instructions into its dynamic memory and send the instructions over a telephone line using a modem. A modem local to computer system 100 can receive the data on the telephone line and use an infra-red transmitter to convert the data to an infra-red signal. An infra-red detector coupled to bus 102 can receive the data carried in the infra-red signal and place the data on bus 102. Bus 102 carries the data to memory 106, from which processor 104 retrieves and executes the instructions. The instructions received by memory 106 may optionally be stored on storage device 110 either before or after execution by processor 104.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

The following descriptions of various implementations of the present teachings have been presented for purposes of illustration and description. It is not exhaustive and does not limit the present teachings to the precise form disclosed. Modifications and variations are possible in light of the above teachings or may be acquired from practicing of the present teachings. Additionally, the described implementation includes software but the present teachings may be implemented as a combination of hardware and software or in hardware alone. The present teachings may be implemented with both object-oriented and non-object-oriented programming systems.

Systems and Methods for Survey Scanning Precursor Ions

As described above, data independent acquisition (DIA) workflows can increase the reproducibility and comprehensiveness of data collection when the complexity and dynamic range of compounds is very large. However, the non-specific nature of these workflows means that product ion data is collected for every nominal mass-to-charge ration (m/z) value in an arbitrary range of values. As a result, for compounds with relatively few precursor ion spread across the mass range, a DIA workflow can be highly inefficient.

In various embodiments, the efficiency of a DIA workflow is improved by performing a full scan ion survey scan using a differential mobility spectrometry (DMS) device. The separation of ions in a DMS device is based upon differences in their migration rates under high versus low electric fields. A high field is applied between the electrodes for a short period of time, and then a low field is applied in the opposite direction for a long period of time. Any difference between the low-field and high-field mobility of an ion of a compound of interest causes it to migrate towards one of the electrodes. The ion is steered back towards the center-line of the device by the application of a second voltage offset, known as the compensation voltage (CoV), a compound-specific parameter that can be used to selectively filter out all other ions. Rapid switching of the compensation voltage parameter allows the user to concurrently monitor many different compounds. An exemplary DMS device is the SelexION™ from AB SCIEX.

In various embodiments, a full scan ion survey scan is performed using a DMS device to obtain precursor ion m/z intensities for a mass range of m/z values as a function of the CoV. For example, the CoV of a DMS device is varied over time. At each CoV interval, the m/z intensities of the precursor ions transmitted by the DMS device are measured across an m/z range using a mass analyzer. The result is a snapshot of the distribution of precursor ions in a CoV-space. Given that there are relationships between the m/z of a precursor ion and its optimal CoV for DMS transmission, a workflow can automatically be optimized to include precursor ions from a subset of m/z values present at discrete CoV values.

Figure 2:
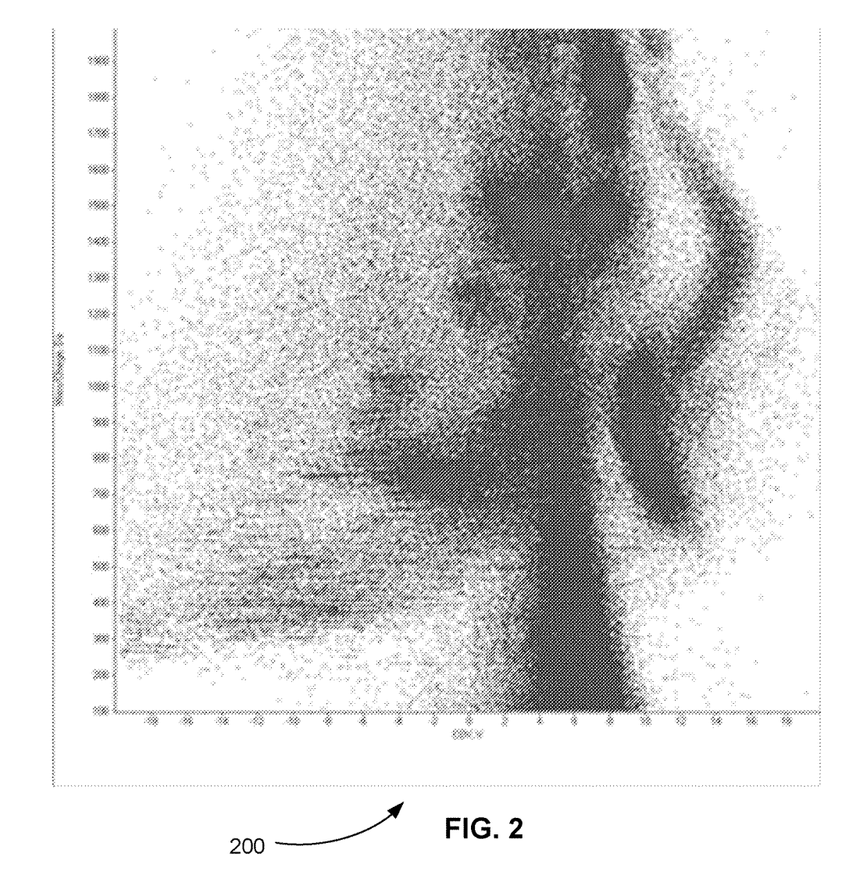
FIG. 2 is an exemplary heat map plot showing the mass-to-charge ratio (m/z) intensities of precursor ions of a sample transmitted by a differential mobility spectrometry (DMS) device as a function of the m/z values of precursor ions and the compensation voltage (CoV) values applied to the DMS device, in accordance with various embodiments.

FIG. 2 is an exemplary heat map plot 200 showing the m/z intensities of precursor ions of a sample transmitted by a DMS device as a function of the m/z values of precursor ions and the CoV values applied to the DMS device, in accordance with various embodiments. Heat map 200 shows that there are tracts of "white space" or areas where little or no useful information would be obtained if all of the precursor ions in the sample were fragmented and the resulting product ions were mass analyzed.

Figure 3:
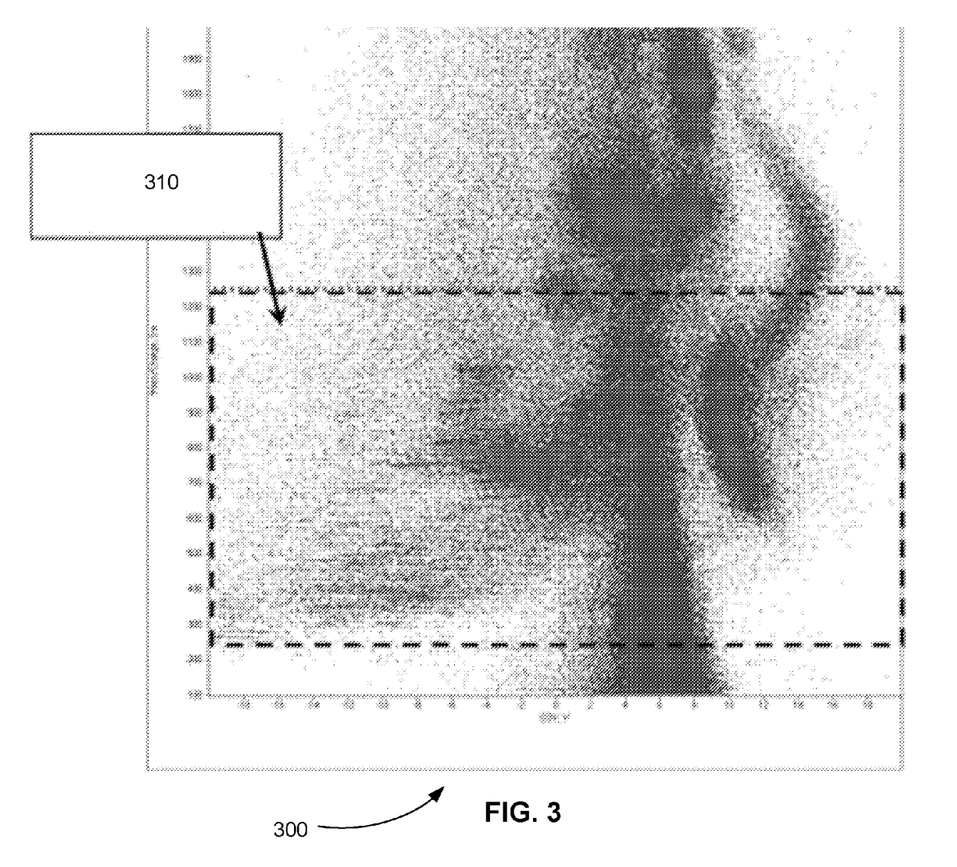
FIG. 3 is an exemplary heat map plot that highlights a region of the same m/z values of precursor ions of a sample transmitted by a DMS device as shown in FIG. 2, in accordance with various embodiments.

FIG. 3 is an exemplary heat map plot 300 that highlights a region 310 of the same m/z values of precursor ions of a sample transmitted by a DMS device as shown in FIG. 2, in accordance with various embodiments. Region 310 includes the m/z values of precursor ions for all CoV values in the m/z range 250 to 1250. Essentially, region 310 shows all the precursor ions in the m/z range that would be fragmented and analyzed in a traditional DIA workflow that did not include a DMS device. FIG. 3 shows that even in the narrower m/z range 250 to 1250 there are tracts of white space where little or no useful information would be obtained by the traditional IDA method.

Figure 4:
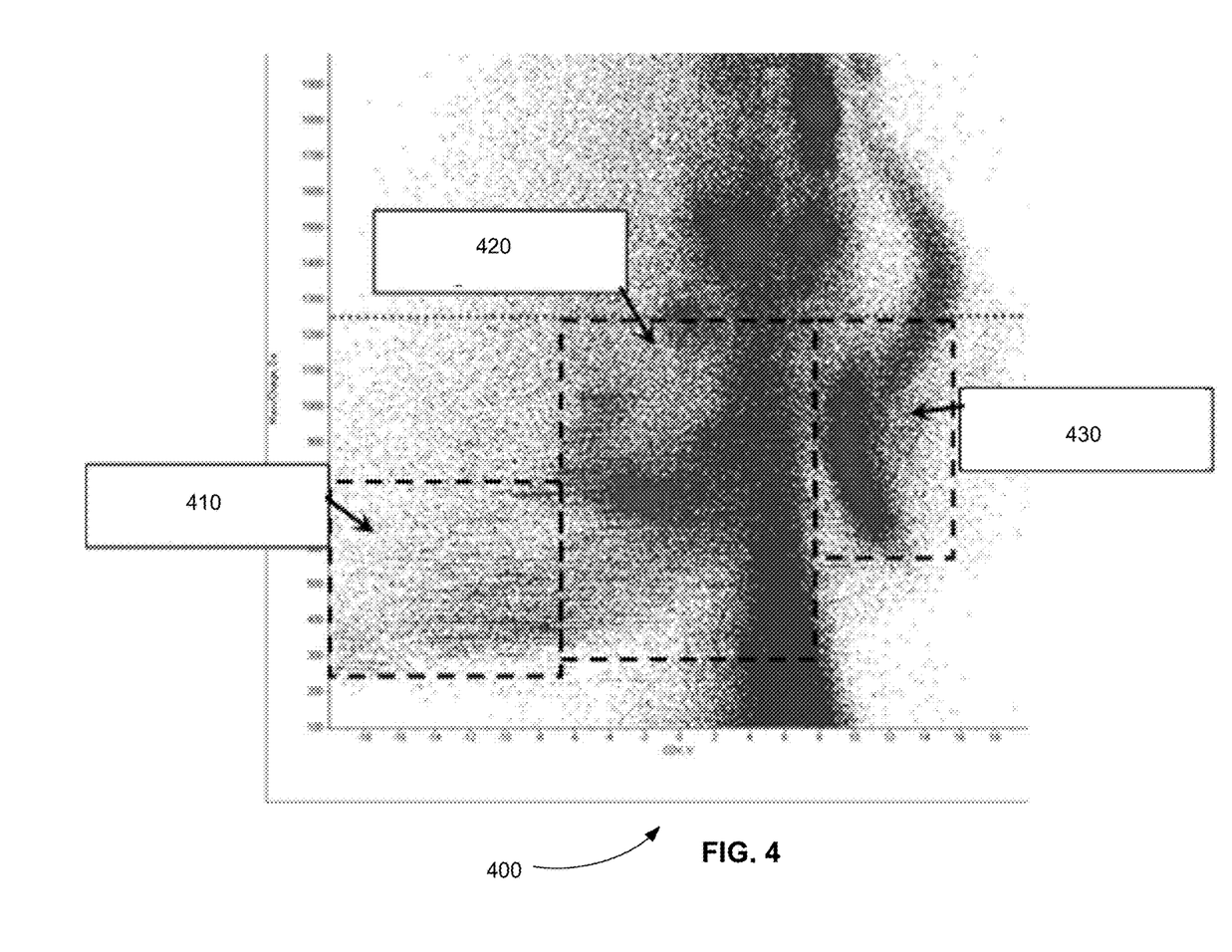
FIG. 4 is an exemplary heat map plot that highlights three regions of the same m/z values of precursor ions of a sample transmitted by a DMS device as shown in FIG. 2, in accordance with various embodiments.

FIG. 4 is an exemplary heat map plot 400 that highlights three regions 410, 420, and 430 of the same m/z values of precursor ions of a sample transmitted by a DMS device as shown in FIG. 2, in accordance with various embodiments. Region 410 includes the m/z values of precursor ions in the m/z range 250 to 800 with CoV values between −30 and −7.0 V. Region 420 includes the m/z values of precursor ions in the m/z range 300 to 1250 with CoV values between −6.5 and +8.0 V. Region 430 includes the m/z values of precursor ions in the m/z range 650 to 1250 with CoV values between +8.0 and +13.0 V. Regions 410, 420, and 430 collectively span the same m/z range spanned by region 310 in FIG. 3. However, regions 410, 420, and 430 do not include all the CoV values. Regions 410, 420, and 430 are used to optimize a DIA workflow so that it includes precursor ions from a subset of m/z values present at discrete CoV values.

Comparing region 310 in FIG. 3 to regions 410, 420, and 430 in FIG. 4 shows that white space can be eliminated in the m/z range 250 to 1250 by selecting 410, 420, and 430 in FIG. 4 rather than region 310 in FIG. 3. Regions 410, 420, and 430 in FIG. 4 are selected, for example, by finding m/z and CoV ranges where m/z values exceed a threshold. Regions 410, 420, and 430 are contiguous and share at least one border. In various embodiments, regions, however, do not have to be contiguous and do not need to share a border.

In various embodiments, the DIA workflow can include additional information provided from the DMS precursor ion survey scan. For example, the DIA workflow can include a dynamic MS/MS accumulation time (based upon the detected intensities of the precursor ions from the DMS precursor ion survey scan), and an optimized collision energy based upon precursor m/z and charge.

In various embodiments, the DMS precursor ion survey scan can be used in conjunction an IDA workflow instead of a DIA workflow. In this scenario, no white space from the m/z versus CoV data is sampled—only analytical ion signal. For example, the DMS precursor ion survey scan (taking ~2 minutes to scan the entire analytical CoV range), contains the analytes' m/z, intensities, and optimal CoV for transmission. Taking this information, an "inclusion list" for subsequent IDA experiments can be generated to maximize the use of the time spent doing MS/MS (acquisition times, etc.).

System for Survey Scanning Precursor Ions

Figure 5:
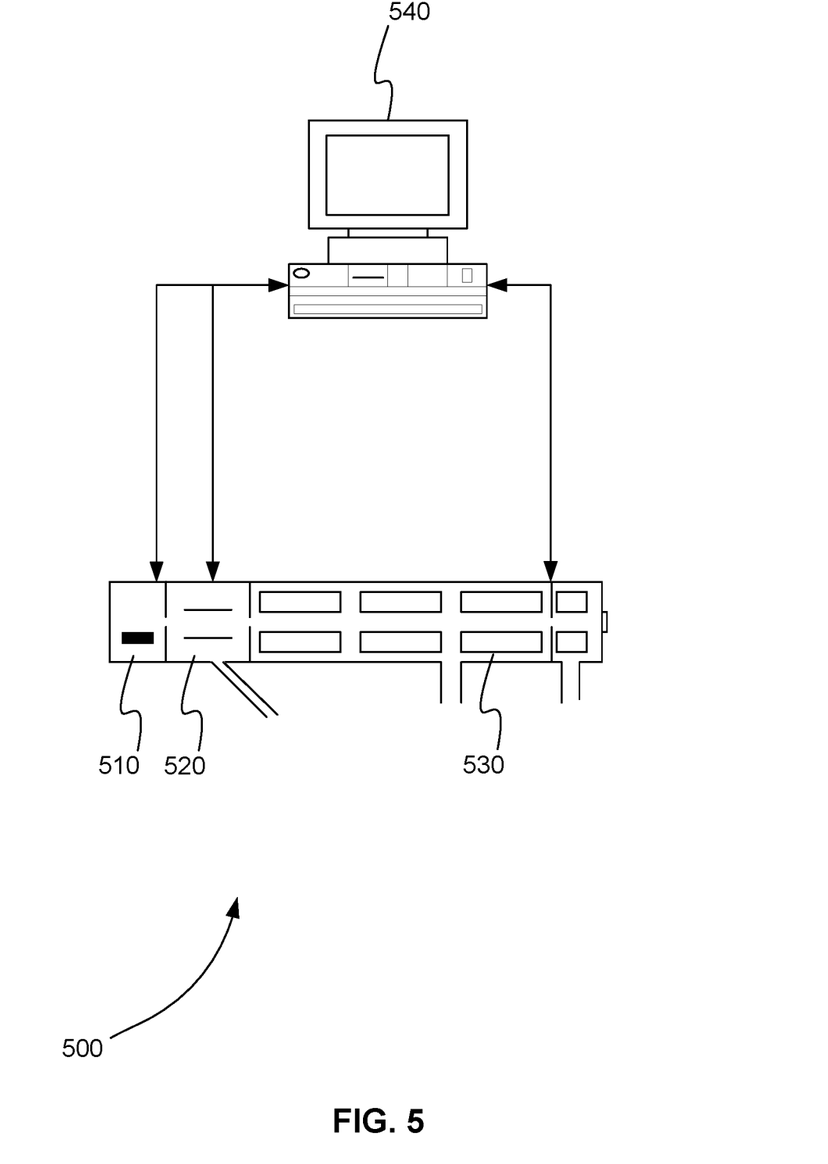
FIG. 5 is a schematic diagram of system for providing a DMS precursor ion survey scan, in accordance with various embodiments.

FIG. 5 is a schematic diagram of system 500 for providing a DMS precursor ion survey scan, in accordance with various embodiments. System 500 includes ion source 510, DMS device 520, mass analyzer 530, and processor 540. Ion source 510 is configured to receive a sample and ionize the sample. DMS device 520 is configured to receive ions from the ion source and to transmit separated precursor ions based on a CoV.

Mass analyzer 530 can be, but is not limited to, a time of flight (TOF), a quadrupole, an ion trap, a linear ion trap, an orbitrap, or a Fourier transform mass analyzer. Mass analyzer 530 can be a standalone device or can be part of a tandem mass spectrometer, for example. Mass analyzer 530 is configured to receive transmitted precursor ions from DMS device 520 and measure the m/z intensities of the transmitted precursor ions.

Processor 540 can be, but is not limited to, a computer, microprocessor, microcontroller, the computer system of FIG. 1, or any device capable of controlling devices, processing data, and sending and receiving data. Processor 540 is in communication with ion source 510, DMS device 520, and mass analyzer 530.

Processor 540 instructs ion source 510 to ionize a sample. Processor 540 instructs DMS device 520 to separate precursor ions received from ion source 510 and transmit precursor ions using two or more CoVs. Processor 540 instructs mass analyzer 530 to measure the m/z intensities of the transmitted precursor ions across an m/z range at each CoV of the two or more CoVs. Finally, processor 540 stores the measured m/z intensities of the transmitted precursor ions received from mass analyzer 530 as a function of m/z value and CoV, producing a two-dimensional mapping of m/z intensities of the transmitted precursor ions of the sample. The two-dimensional mapping of m/z intensities is stored in a memory or storage device, for example.

In various embodiments, processor 540 further selects one or more regions of the stored two-dimensional mapping where m/z intensities of the transmitted precursor ions exceed a predetermined threshold for use in a DIA tandem mass spectrometry workflow. The CoV by m/z map is a form of a two dimensional image. Any of a number of image segmentation techniques could be used to automatically detect regions of high precursor intensity. These techniques include, but are not limited to: thresholding, clustering, and edge detection. Each region of the one or more regions is defined by an m/z range and a CoV range within the two-dimensional mapping.

As described by wikipedia, image segmentation is the process of partitioning a digital image into multiple segments (sets of pixels, also known as superpixels). http://en.wikipedia.org/wiki/Image_segmentation. The goal of segmentation is to simplify and/or change the representation of an image into something that is more meaningful and easier to analyze. Id. Image segmentation is typically used to locate objects and boundaries (lines, curves, etc.) in images. Id. More precisely, image segmentation is the process of assigning a label to every pixel in an image such that pixels with the same label share certain characteristics. Id. The result of image segmentation is a set of segments that collectively cover the entire image, or a set of contours extracted from the image (see edge detection). Id. Each of the pixels in a region are similar with respect to some characteristic or computed property, such as color, intensity, or texture. Adjacent regions are significantly different with respect to the same characteristic(s). Id. When applied to a stack of images, typical in medical imaging, the resulting contours after image segmentation can be used to create 3D reconstructions with the help of interpolation algorithms like marching cubes. Id. The simplest method of image segmentation is called the thresholding method. Id. This method is based on a clip-level (or a threshold value) to turn a gray-scale image into a binary image. Id. There is also a balanced histogram thresholding. Id. The key of this method is to select the threshold value (or values when multiple-levels are selected). Id. Several popular methods are used in industry including the maximum entropy method, Otsu's method (maximum variance), and k-means clustering. Id.

In various embodiments, processor 540 further calculates a dynamic MS/MS accumulation time for each region of the one or more region based on the m/z intensities of the transmitted precursor ions in each region and calculates an optimized collision energy for each region of the one or more region based on the m/z values of the transmitted precursor ions in each region.

In various embodiments, processor 540 further selects each m/z intensity of each transmitted precursor ion of the stored two-dimensional mapping that exceeds a predetermined threshold (of intensity, or signal to noise) and adds the m/z value and CoV of the m/z intensity that exceeds a predetermined threshold to an inclusion list for use in an IDA tandem mass spectrometry workflow.

In various embodiments, processor 540 further calculates a dynamic MS/MS accumulation time for each transmitted precursor ion of the stored two-dimensional mapping based on the m/z intensity of the each transmitted precursor ion and calculates an optimized collision energy for the each transmitted precursor ion based on the m/z values of the each transmitted precursor ion.

Method for Survey Scanning Precursor Ions

Figure 6:
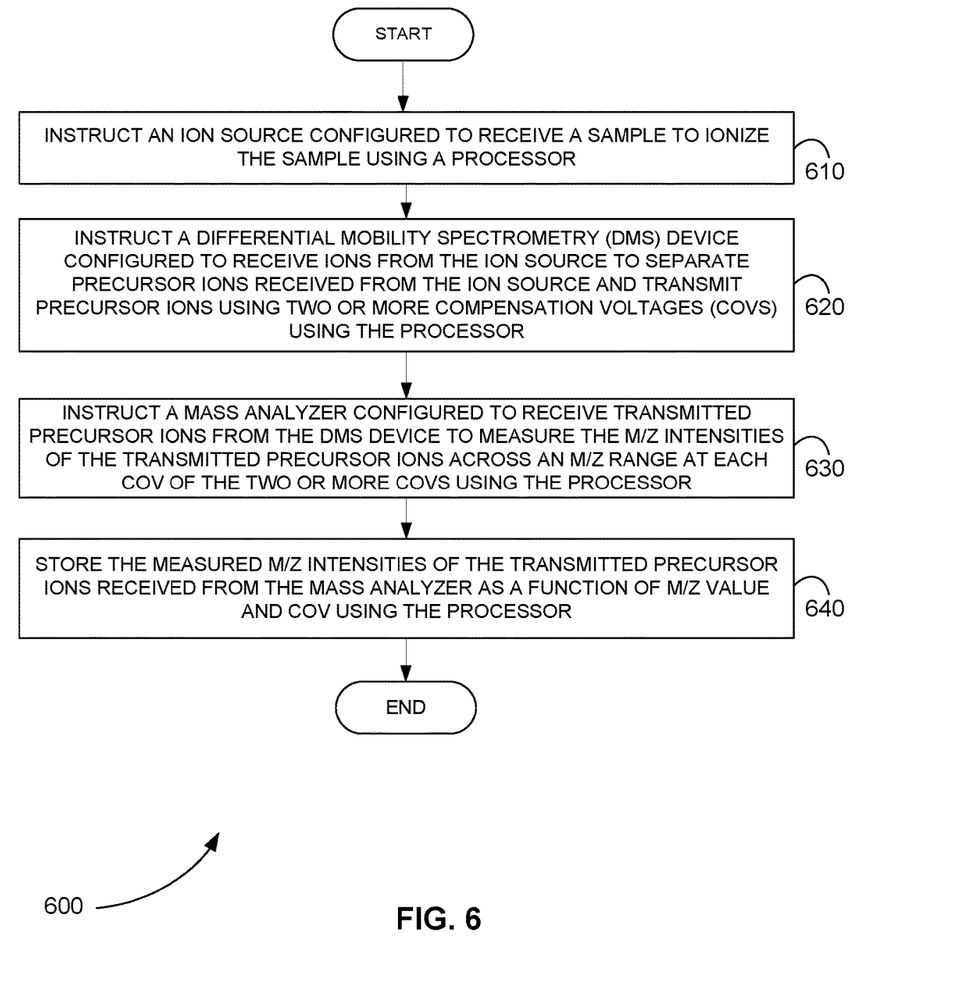
FIG. 6 is a flowchart showing a method for providing a DMS precursor ion survey scan, in accordance with various embodiments.

FIG. 6 is a flowchart showing a method 600 for providing a DMS precursor ion survey scan, in accordance with various embodiments.

In step 610 of method 600, an ion source configured to receive a sample is instructed to ionize the sample using a processor.

In step 620, a DMS device configured to receive ions from the ion source is instructed to separate precursor ions received from the ion source and transmit precursor ions using two or more CoVs using the processor.

In step 630 a mass analyzer configured to receive transmitted precursor ions from the DMS device is instructed to measure the m/z intensities of the transmitted precursor ions across an m/z range at each CoV of the two or more CoVs using the processor.

In step 640, the measured m/z intensities of the transmitted precursor ions received from the mass analyzer are stored as a function of m/z value and CoV using the processor. This produces a stored two-dimensional mapping of m/z intensities of the precursor ions of the sample.

Computer Program Product for Survey Scanning Precursor Ions

In various embodiments, computer program products include a tangible computer-readable storage medium whose contents include a program with instructions being executed on a processor so as to perform a method for providing a DMS precursor ion survey scan. This method is performed by a system that includes one or more distinct software modules.

Figure 7:
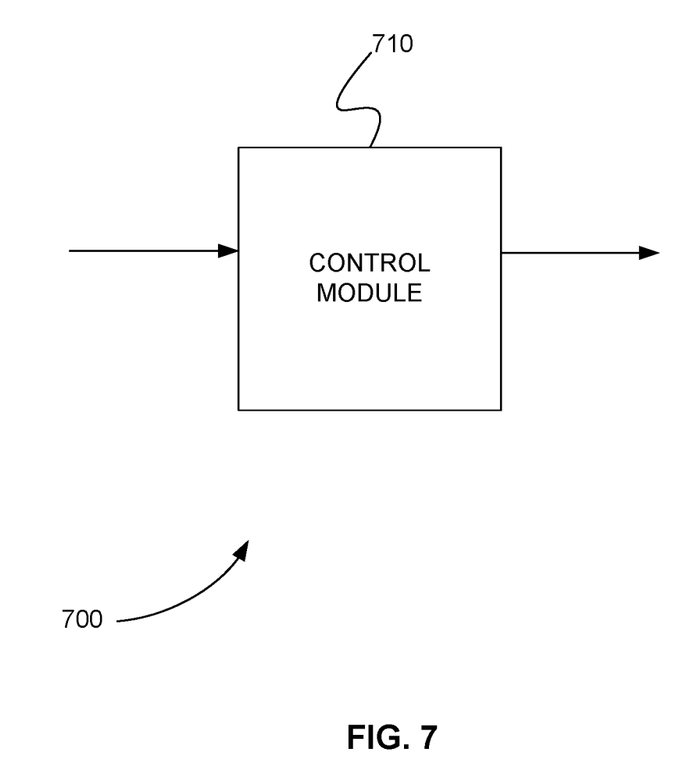
FIG. 7 is a schematic diagram of a system that includes one or more distinct software modules that performs a method for providing a DMS precursor ion survey scan, in accordance with various embodiments.

FIG. 7 is a schematic diagram of a system 700 that includes one or more distinct software modules that performs a method for providing a DMS precursor ion survey scan, in accordance with various embodiments. System 700 includes control module 710.

Control module 710 instructs an ion source configured to receive a sample to ionize the sample. Control module 710 instructs a DMS device configured to receive ions from the ion source to separate precursor ions received from the ion source and transmit precursor ions using two or more CoVs. Control module 710 instructs a mass analyzer configured to receive transmitted precursor ions from the DMS device to measure the m/z intensities of the transmitted precursor ions across an m/z range at each CoV of the two or more CoVs. Control module 710 stores the measured m/z intensities of the transmitted precursor ions received from the mass analyzer as a function of m/z value and CoV, producing a two-dimensional mapping of m/z intensities of the precursor ions of the sample.

One of ordinary skill in the art can appreciate that the use of the term "mass" used herein is interchangeable with the term "mass-to-charge ratio (m/z)".

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

What is claimed is:

1. A system for providing a differential mobility spectrometry (DMS) precursor ion survey scan, comprising:
   an ion source configured to receive a sample and ionize the sample;
   a differential mobility spectrometry (DMS) device configured to receive ions from the ion source and to transmit separated precursor ions based on a compensation voltage (CoV);
   a mass analyzer configured to receive transmitted precursor ions from the DMS device and measure the mass-to-charge ratio (m/z) intensities of the transmitted precursor ions; and
   a processor in communication with the ion source, the DMS device, and the mass analyzer that
      instructs the ion source to ionize the sample,
      instructs the DMS device to separate precursor ions received from the ion source and transmit precursor ions using two or more CoVs,
      instructs the mass analyzer to measure the m/z intensities of the transmitted precursor ions across an m/z range at each CoV of the two or more CoVs, and
      stores the measured m/z intensities of the transmitted precursor ions received from the mass analyzer as a function of m/z value and CoV, producing a two-dimensional mapping of m/z intensities of the transmitted precursor ions of the sample.

2. The system of claim 1, wherein the processor further selects one or more regions of the stored two-dimensional mapping where m/z intensities of the transmitted precursor ions exceed a predetermined threshold for use in a data independent acquisition (DIA) tandem mass spectrometry workflow, wherein each region of the one or more regions is defined by an m/z range and a CoV range.

3. The system of claim 2, wherein the processor further calculates a dynamic mass spectrometry/mass spectrometry (MS/MS) accumulation time for each region of the one or more region based on the m/z intensities of the transmitted precursor ions in each region and calculates an optimized collision energy for each region of the one or more region based on the m/z values of the transmitted precursor ions in each region.

4. The system of claim 1, wherein the processor further selects each m/z intensity of each transmitted precursor ion of the stored two-dimensional mapping that exceeds a predetermined threshold and adds the m/z value and CoV of the m/z intensity that exceeds a predetermined threshold to an inclusion list for use in an information dependent acquisition (IDA) tandem mass spectrometry workflow.

5. The system of claim 4, wherein the processor further calculates a dynamic mass spectrometry/mass spectrometry (MS/MS) accumulation time for each transmitted precursor ion of the stored two-dimensional mapping based on the m/z intensity of the each transmitted precursor ion and calculates an optimized collision energy for the each transmitted precursor ion based on the m/z values of the each transmitted precursor ion.

6. A method for providing a differential mobility spectrometry (DMS) precursor ion survey scan, comprising:
   instructing an ion source configured to receive a sample to ionize the sample using a processor;
   instructing a differential mobility spectrometry (DMS) device configured to receive ions from the ion source to separate precursor ions received from the ion source and transmit precursor ions using two or more compensation voltages (CoVs) using the processor;

instructing a mass analyzer configured to receive transmitted precursor ions from the DMS device to measure the m/z intensities of the transmitted precursor ions across an m/z range at each CoV of the two or more CoVs using the processor; and storing the measured m/z intensities of the transmitted precursor ions received from the mass analyzer as a function of m/z value and CoV, producing a two-dimensional mapping of m/z intensities of the precursor ions of the sample using the processor.

7. The method of claim 6, further comprising selecting one or more regions of the stored two-dimensional mapping where m/z intensities of the transmitted precursor ions exceed a predetermined threshold for use in a data independent acquisition (DIA) tandem mass spectrometry workflow using the processor, wherein each region of the one or more regions is defined by an m/z range and a CoV range.

8. The method of claim 7, further comprising calculating a dynamic mass spectrometry/mass spectrometry (MS/MS) accumulation time for each region of the one or more region based on the m/z intensities of the transmitted precursor ions in each region and calculating an optimized collision energy for each region of the one or more region based on the m/z values of the transmitted precursor ions in each region using the processor.

9. The method of claim 6, further comprising selecting each m/z intensity of each transmitted precursor ion of the stored two-dimensional mapping that exceeds a predetermined threshold and adding the m/z value and CoV of the m/z intensity that exceeds a predetermined threshold to an inclusion list for use in an information dependent acquisition (IDA) tandem mass spectrometry workflow using the processor.

10. The method of claim 9, further comprising calculating a dynamic mass spectrometry/mass spectrometry (MS/MS) accumulation time for each transmitted precursor ion of the stored two-dimensional mapping based on the m/z intensity of the each transmitted precursor ion and calculating an optimized collision energy for the each transmitted precursor ion based on the m/z values of the each transmitted precursor ion using the processor.

11. A computer program product, comprising a non-transitory and tangible computer-readable storage medium whose contents include a program with instructions being executed on a processor so as to perform a method for providing a differential mobility spectrometry (DMS) precursor ion survey scan, the method comprising:

providing a system, wherein the system comprises one or more distinct software modules, and wherein the distinct software modules comprise a control module;

instructing an ion source configured to receive a sample to ionize the sample using the control module;

instructing a differential mobility spectrometry (DMS) device configured to receive ions from the ion source to separate precursor ions received from the ion source and transmit precursor ions using two or more compensation voltages (CoVs) using the control module;

instructing a mass analyzer configured to receive transmitted precursor ions from the DMS device to measure the m/z intensities of the transmitted precursor ions across an m/z range at each CoV of the two or more CoVs using the control module; and storing the measured m/z intensities of the transmitted precursor ions received from the mass analyzer as a function of m/z value and CoV, producing a two-dimensional mapping of m/z intensities of the precursor ions of the sample using the control module.

12. The computer program product of claim 11, further comprising selecting one or more regions of the stored two-dimensional mapping where m/z intensities of the transmitted precursor ions exceed a predetermined threshold for use in a data independent acquisition (DIA) tandem mass spectrometry workflow using the control module, wherein each region of the one or more regions is defined by an m/z range and a CoV range.

13. The computer program product of claim 12, further comprising calculating a dynamic mass spectrometry/mass spectrometry (MS/MS) accumulation time for each region of the one or more region based on the m/z intensities of the transmitted precursor ions in each region and calculating an optimized collision energy for each region of the one or more region based on the m/z values of the transmitted precursor ions in each region using the control module.

14. The computer program product of claim 11, further comprising selecting each m/z intensity of each transmitted precursor ion of the stored two-dimensional mapping that exceeds a predetermined threshold and adding the m/z value and CoV of the m/z intensity that exceeds a predetermined threshold to an inclusion list for use in an information dependent acquisition (IDA) tandem mass spectrometry workflow using the control module.

15. The computer program product of claim 14, further comprising calculating a dynamic mass spectrometry/mass spectrometry (MS/MS) accumulation time for each transmitted precursor ion of the stored two-dimensional mapping based on the m/z intensity of the each transmitted precursor ion and calculating an optimized collision energy for the each transmitted precursor ion based on the m/z values of the each transmitted precursor ion using the control module.

* * * * *